US008697135B2

(12) United States Patent
Jepsen (10) Patent No.: US 8,697,135 B2
(45) Date of Patent: Apr. 15, 2014

(54) METHOD FOR THE PREPARATION OF A PHARMACEUTICAL COMPOSITION COMPRISING 5-AMINOSALICYLIC ACID FOR USE IN TREATMENT OF ULCERATIVE COLITIS AND CROHN'S DISEASE

(75) Inventor: Svenn Klüver Jepsen, Holte (DK)

(73) Assignee: Ferring B.V., Hoofddorp (NL)

(*) Notice: Subject to any disclaimer, the term of this patent is extended or adjusted under 35 U.S.C. 154(b) by 0 days.

(21) Appl. No.: 13/606,443

(22) Filed: Sep. 7, 2012

(65) Prior Publication Data

US 2013/0195980 A1 Aug. 1, 2013

Related U.S. Application Data

(62) Division of application No. 10/269,055, filed on Oct. 11, 2002, now Pat. No. 8,282,955.

(60) Provisional application No. 60/328,831, filed on Oct. 15, 2001.

(30) Foreign Application Priority Data

Oct. 15, 2001 (WO) ...................... PCT/DK01/00677

(51) Int. Cl.
*A61K 9/50* (2006.01)

(52) U.S. Cl.
USPC ......................................................... 424/497

(58) Field of Classification Search
USPC ......................................................... 424/497
See application file for complete search history.

(56) References Cited

U.S. PATENT DOCUMENTS

| | | | |
|---|---|---|---|
| 3,758,563 A | 9/1973 | Uematsu et al. |
| 4,632,921 A | 12/1986 | Bauer |
| 4,880,794 A | 11/1989 | Halskov |
| 4,960,765 A | 10/1990 | Halskov |
| 4,980,173 A | 12/1990 | Halskov |
| 5,013,727 A | 5/1991 | Halskov |
| 5,188,841 A | 2/1993 | Simpkin et al. |
| 5,194,464 A | 3/1993 | Itoh et al. |
| 5,254,347 A | 10/1993 | Samejima et al. |
| 5,316,772 A | 5/1994 | Jurgens et al. |
| 5,472,712 A | 12/1995 | Oshlack et al. |
| 5,482,718 A | 1/1996 | Shah et al. |
| 5,484,605 A | 1/1996 | Scheiffele et al. |
| 5,541,170 A | 7/1996 | Rhodes et al. |
| 6,004,581 A | 12/1999 | Jepsen |
| 6,245,351 B1 | 6/2001 | Nara et al. |
| 6,773,720 B1 | 8/2004 | Villa et al. |
| 7,022,345 B2 | 4/2006 | Valducci |
| 8,282,955 B2 | 10/2012 | Jepsen |
| 8,282,958 B2 | 10/2012 | Jepsen |
| 8,501,226 B2 | 8/2013 | Jepsen |
| 2001/0046964 A1 | 11/2001 | Percel et al. |
| 2002/0177579 A1 | 11/2002 | Augsburger et al. |
| 2006/0006258 A1 | 1/2006 | Remon et al. |
| 2007/0043004 A1 | 2/2007 | Jepsen |

FOREIGN PATENT DOCUMENTS

| | | |
|---|---|---|
| DE | 100 13 030 | 9/2001 |
| EP | 0 148 811 | 7/1985 |
| EP | 0 540 813 B1 | 3/1996 |
| EP | 1004297 | 5/2000 |
| EP | 1172100 | 1/2002 |
| GB | 2 163 957 A | 3/1986 |
| JP | 57-11912 | 1/1982 |
| JP | 57-58631 | 4/1982 |
| JP | 08026977 A | 1/1996 |
| JP | 2001-55322 | 2/2001 |
| WO | WO 91/16042 A1 | 10/1991 |
| WO | WO 92/11001 A1 | 7/1992 |
| WO | WO 92/14452 A1 | 9/1992 |
| WO | WO 97/23199 | 7/1997 |
| WO | WO 98/03161 | 1/1998 |
| WO | WO 98/04321 A1 | 2/1998 |
| WO | WO 98/26767 A1 | 6/1998 |
| WO | WO 99/21536 A1 | 5/1999 |
| WO | WO 01/66094 A1 | 9/2001 |

OTHER PUBLICATIONS

U.S. Appl. No. 13/956,733, filed Aug. 1, 2013, Jepsen.
Office Action issued on Feb. 19, 2010 in U.S. Appl. No. 10/553,629 (US 2007/0043004).
Office Action issued on Apr. 17, 2009 in U.S. Appl. No. 10/553,629 (US 2007/0043004).
Office Action issued on Nov. 13, 2008 in U.S. Appl. No. 10/553,629 (US 2007/0043004).
Office Action issued on Feb. 7, 2008 in U.S. Appl. No. 10/553,629 (US 2007/0043004).
Gupta et al., :"A novel pH- and time-based multi-unit potential colonic drug delivery system," International Journal of Pharmaceutics, vol. 213, pp. 83-91, 2001.
Klein et al., "Drug Release Characteristics of Different Mesalazine Products Using USP Apparatus 3 to Simulate Passage Through the GI Tract," Dissolution Technologies, pp. 1-8, Nov. 2002.
French et al., "Evaluation of the Physicochemical Properties and Dissolution Characteristics of Mesalamine: Relevance to Controlled Intestinal Drug Delivery," Pharmaceutical Research, vol. 10, No. 9, 1993.
Percev et al., ed., "NFAY," Farmatesevticheskie I medico-biologicheskie aspekty lekarstv, Kharkov, vol. 2, pp. 360-362, 1999.
Chueshov, "Promyshlennaja technologija lekarstv," vol. 2, pp. 383-392, 1999.
Gamlen et al., "Continuous Extrusion Using a Baker Perkins MP50 (Multipurpose) Extruder," Drug Development and Industrial Pharmacy, vol. 12, No. 11-13, pp. 1701-1713, 1986.
Millili et al., "The Strength of Microcrystalline Cellulose Pellets: The Effect of Granulating with Water/Ethanol Mixtures," Drug Development and Industrial Pharmacy, vol. 16, No. 8, pp. 1411-1426, 1990.
Merck, "Povidone," The Merck Index, p. 1320, 1996.

(Continued)

*Primary Examiner* — Jake Vu
(74) *Attorney, Agent, or Firm* — Foley & Lardner LLP (57) ABSTRACT

The present invention concerns a new method of preparing granules comprising 5-aminosalicylic acid and a new method of preparing a pharmaceutical composition for the treatment of ulcerative colitis or Crohn's disease by oral administration comprising as active ingredient 5-aminosalicylic acid.

10 Claims, 9 Drawing Sheets

(56) References Cited

OTHER PUBLICATIONS

Merriam-Webster, "derivative," Merriam-Webster's Collegiate Dictionary, p. 311, 1993.
Office Action issued on Mar. 31, 2004 by the Examiner in U.S. Appl. No. 10/269,055 (US 2003/0138495).
Office Action issued on Sep. 9, 2005 by the Examiner in U.S. Appl. No. 10/269,055 (US 2003/0138495).
Office Action issued on May 17, 2006 by the Examiner in U.S. Appl. No. 10/269,055 (US 2003/0138495).
Office Action issued on Dec. 29, 2006 by the Examiner in U.S. Appl. No. 10/269,055 (US 2003/0138495).
Office Action issued on Sep. 20, 2007 By the Examiner in U.S. Appl. No. 10/269,055 (US 2003/0138495).
Office Action issued on May 28, 2008 by the Examiner in U.S. Appl. No. 10/269,055 (US 2003/0138495).
Office Action issued on Nov. 19, 2008 by the Examiner in U.S. Appl. No. 10/269,055 (US 2003/0138495).
Office Action issued on Jul. 31, 2009 by the Examiner in U.S. Appl. No. 10/269,055 (US 2003/0138495).
Office Action issued on Apr. 19, 2010 by the Examiner in U.S. Appl. No. 10/269,055 (US 2003/0138495).
Office Action issued on Nov. 9, 2010 by the Examiner in U.S. Appl. No. 10/269,055 (US 2003/0138495).
Office Action issued on Jul. 7, 2011 by the Examiner in U.S. Appl. No. 10/269,055 (US 2003/0138495).
Office Action issued on Oct. 3, 2011 by the Examiner in U.S. Appl. No. 10/269,055 (US 2003/0138495).
Office Action issued on Dec. 20, 2011 by the Examiner in U.S. Appl. No. 10/269,055 (US 2003/0138495).
Notice of Allowance issued on Jun. 7, 2012 by the Examiner in U.S. Appl. No. 10/269,055 (US 2003/0138495).

Fig. 1A Batch no.: KGGU 405R

Fig 1B

Fig 2A Batch no.: KGGU 406Q

FIG. 2B

Fig. 3A Batch no.: KGGU 406T

Fig. 5A Batch no : HLGU 311

Fig. 5B

Fig. 6A Batch no.: HLGU 315

Fig 6B

Fig. 7A Batch no.: HLGU 319

METHOD FOR THE PREPARATION OF A PHARMACEUTICAL COMPOSITION COMPRISING 5-AMINOSALICYLIC ACID FOR USE IN TREATMENT OF ULCERATIVE COLITIS AND CROHN'S DISEASE

The present invention relates to a method of preparing a pharmaceutical composition useful for the treatment of ulcerative colitis and Crohn's disease, currently denominated "inflammatory bowel diseases" (IBD). More particular, the invention relates to a new method of producing granules comprising 5-aminosalicylic acid (5-ASA) for use in the preparation of solid oral dosage forms.

Ulcerative colitis is a chronic inflammatory disease of the colon of unknown etiology. In its acute stages it resembles an infectious disease, but no microorganism has been definitively established as its cause. The disease causes inflammations of the mucosa of the colon, with extension to the submucosa in severe cases. Typically, not only the colon, but also the rectum is attacked, but only rarely is the ileum involved. The ulcer formation and its extent vary with the developmental stage of the disease, but can often be determined macroscopically (sigmoidoscopy and colonoscopy).

The related disease, Crohn's disease, also known as regional enteritis or colitis granulomatosa, is most frequently located in the small intestine (small bowel), especially in the ileum, but may also affect the jejunum and any part of the colon, including the rectum. In the latter case the differentiation of Crohn's disease from ulcerative colitis gives rise to great diagnostic problems. Generally, the inflammation differs from that of ulcerative colitis by progressing to layers deeper than the mucosa and affecting the epithelium to a lesser degree.

Both diseases have become increasingly frequent especially in the developed countries. In the United States, the incidence of the ulcerative colitis is 5-15 cases per 100,000 inhabitants, whereas the incidence is approximately 5 per 100,000 inhabitants in the case of Crohn's disease, the figures continue to increase. Therefore, treatment of IBD has become an important problem of modern medicine.

WO 81/02671 discloses a pharmaceutical composition for the treatment of IBD by oral administration. The invention was based on findings that an oral administration of 5-ASA as the free acid or in the form of its salts or esters has a useful therapeutic effect on ulcerative colitis, in particular when administered in the form of sustained-release tablets. WO 81/02671 further discloses a method for the preparation of sustained release tablets comprising the steps of preparing granules from 5-ASA and a solution of polyvinylpyrrolidone in isopropanol, evaporating the solvent, coating the granules with ethyl cellulose and formulating the coated granules into tablets.

U.S. Pat. No. 4,632,921 further discloses a process for the production of readily soluble 5-ASA preparations by mixing 5-ASA with physiologically and toxicologically acceptable, basic auxiliaries and/or buffer mixtures, which in a 1% aqueous solution give pH-values in the range from 8 to 12, and the mixture obtained is processed in known manner to form tablets, film tablets, dragees, capsules or suppositories, i.e. a stable and readily soluble pharmaceutical preparation for oral or rectal application based on 5-ASA for use in the treatment of IBD.

U.S. Pat. No. 4,880,794 discloses a method for the treatment of IBD comprising orally administering an effective amount of a composition consisting essentially of a pharmaceutically acceptable salt of free 5-ASA in admixture with a pharmaceutically acceptable carrier which will control the release of said effective amount of said salt of 5-ASA to be administered according to the actual site of said disease.

U.S. Pat. No. 4,960,765 further discloses a method for the treatment of IBD comprising orally administering an effective amount of a composition consisting essentially of an ester of free 5-ASA in admixture with a pharmaceutically acceptable carrier so as to delay the release of 5-ASA from said composition essentially until it reaches the colon of the patient. Release dependent on pH in the colon is achieved by using a coating resulting in a gradual release of 5-ASA. The particles are coated with ethyl cellulose.

U.S. Pat. No. 4,980,173 discloses a method for the preparation of sustained-release tablets useful for the treatment of IBD by preparing a granulate containing 5-ASA and PVP using an organic solvent. The granulate is coated with a pH sensitive coating (cellulose derivative). A second non-coated granulate is prepared and mixed with the coated granulate and a lubricant.

U.S. Pat. No. 5,013,727 discloses a pharmaceutical composition containing as active ingredient 5-ASA or a pharmaceutically acceptable salt or ester thereof allowing the treatment of IBD by oral administration. A particular slow-release tablet formulation and its preparation are disclosed.

U.S. Pat. No. 5,541,170 further discloses a pharmaceutical composition and method for the treatment of IBD by oral administration. The invention may be a solid dosage form, such as a capsule or tablet, containing a pharmacologically active agent coated with an anionic polymer, which is insoluble in gastric juice and in intestinal juice below pH 7 but soluble in colonic intestinal juice, in a sufficient amount that the oral dosage form remains intact until it reaches the colon. The preferred anionic polymer is a partly methyl esterified methacrylic acid polymer in which the ratio of free carboxylic groups to ester groups is about 1:2. The invention has particular application to dosage forms of prednisolone and salts thereof, indomethacin, ibuprofen, and, especially, 5-aminosalicylic acid.

5-ASA has proven to be very useful in treating ulcerative colitis and Crohn's disease. Different 5-ASA prolonged release 250 mg and later on 500 mg tablets, e.g. Pentasa®, have been registered in different countries for a number of years.

All the prior art concerning 5-ASA tablet formulations disclose the use of isopropyl alcohol as the main solvent for the binder in the preparation of 5-ASA granules. It is nowhere disclosed that another solvent, such as water, for the purpose of producing tablets, may replace the organic solvent.

WO 97/23199 discloses a modified release composition for treatment of IBD comprising spherical granules comprising a core of 5-ASA and a spheronisation aid prepared in water as a solvent and coated with a rate limiting barrier material. The composition results in a minor release of 5-ASA in the stomach and the granules may be packed in sachets. These granules are not suitable for use in tablets.

Due to the still increasing demand for 5-ASA containing pharmaceuticals, there is a need for improving the manufacturing process of 5-ASA containing tablets.

SUMMARY OF THE INVENTION

As each 5-ASA containing tablet or dose contains a relative large amount of the active ingredient in order to maximise the therapeutic effect, large amounts of material have to be handled at the production facilities.

The ever-growing market for 5-ASA containing medicaments has lead to a demand for improvements of the hitherto used method for the production of 5-ASA-containing tablets.

In the present invention, the improvements provide for a better, faster and less costly method for the production of 5-ASA containing tablets without loss of quality and bioavailability of the 5-ASA.

The aim of the invention is to obtain an improved composition of extruded granules for use in Pentasa® or similar tablets. The granules should be strong and smooth, tolerate the different processing steps during production and be produced with a narrow and reproducible particle size distribution.

Surprisingly, an improvement could be achieved without changing the main principle in the existing manufacturing process.

5-ASA comprising tablets prepared according to the present invention are still produced by first mixing the active ingredient 5-aminosalicylic acid with a solution of a pharmaceutically acceptable binder, e.g. polyvinylpyrrolidone (PVP), in a solvent. This mixture is extruded into granules, which are dried in a fluid bed. After drying the granules are milled and sieved before the granules are ready for coating, for example in a fluid bed. In the coating process a polymer is coated upon the granules until the desired dissolution rate profile is obtained. The coated granules are then mixed with tablet excipients and compressed into tablets.

In one aspect of the invention, it has surprisingly been found that the organic solvent used in the existing method may advantageously be replaced partly or totally by water.

U.S. Pat. Re 33,239 teaches that 5-ASA has a poor stability being sensitive to moisture and light. Said patent discloses a pharmaceutical composition comprising 5-ASA in solution or as a suspension together with additives in order to stabilise the 5-ASA. Moreover, the composition is to be packed in a diffusion tight light-impervious package under an inert gas.

Thus, the use of water as the main solvent is contrary to the teaching concerning formulation of 5-ASA tablets. In the existing method, the problem with stability related to moisture is avoided by the use of an organic solvent as the main solvent. Surprisingly, it has now turned out that water may indeed be used as the major part of the solvent in the preparation of granules containing 5-ASA for use in tablet formulations, essentially without affecting the stability of 5-ASA. It is believed that the use of a continuous drying process in e.g. a fluid bed is instrumental for obtaining a stable product allowing for a quick and gentle drying process as well as protecting the product against light.

In WO 97/23199 water was used as a solvent in the production of the spherical granules, which, however, comprise a different binder and are treated immediately in a spheronisation and drying process. The spherical granules are not optimal for use in tablets due to segregation.

It has now surprisingly turned out that replacement of all or a part of the organic solvent by water leads to a process in which granules with a narrower particle size distribution are produced and that the resulting granules are stronger with a smoother surface. These improvements lead to an increased yield of tablets from the process. Furthermore, the smooth surface of the granules results in the coating process becoming more reproducible and reduces the amount of coating material used in the process.

In addition to the above improvements of the product, a reduction in the use of organic solvents is the result, leading to a reduced hazard to the operators in the production facilities and to the environment as well as a reduction in the overall content of organic solvent in the final product. Additionally, the costs of organic solvents may be highly reduced.

In a second aspect of the present invention, the preparation of granules from the wet mass of 5-ASA and the binder form part of a continuous production line for the production of 5-ASA granules.

In a third aspect of the present invention, the method of preparing granules forms part of a method of preparing 5-ASA tablets.

As discussed above, it may be desirable to handle large amounts of material in the production line. The production line may therefore advantageously be designed to be continuous, where 5-ASA is mixed with the aqueous PVP solution before or in the extruder, and the resulting granules are dried, milled and sieved in one continuous process. The feeding of the individual ingredients is regulated continuously, e.g. by way of weight measurements of the different feeds as a part of the production line.

DETAILED DESCRIPTION OF THE INVENTION

The present invention concerns a new method for the preparation of 5-ASA granules and a new method of producing 5-ASA containing tablets.

The present invention has led to improvements in the overall manufacturing process of tablets, but also in the production of 5-ASA containing granules, improvements that were desired according to the aim of the invention, but which means for success were neither expected, nor foreseeable. There are no indications in the prior art that replacement of the organic solvent by water could fulfil the aim of the invention and thus lead to the desired improvements. The method according to the prior art teaches the use of a solvent comprising about 90% w/w isopropanol and 10% w/w water.

According to the present invention, the solvent suitable for dissolution of the binder is based on water. The solvent contains at least 50% w/w water, preferably at least 85% w/w water, more preferably at least 95% w/w and most preferably 100% w/w. The remaining part of the solvent may be any suitable liquid, such as an organic solvent. The solvent may also comprise additives of importance for the process or final product. Such additives are within the knowledge of the skilled person. Examples are chelating agents, antioxidants, reducing agents, buffers, pH adjuring agents, cosolvents or any other relevant excipients. Organic solvents may be present in minor amount as a solubilising agent for the additives. Preferably the solvent is free of organic solvent.

As each tablet contains a high dose of the active ingredient, 5-aminosalicylic acid, it is desirable to handle large amounts of material at the production facility. The aim of the present invention is thus to improve the existing process, whereby more tablets can be produced at lower costs, and without compromising on the quality of the product.

The main focus of the invention has been to find a method by which it is possible to obtain granules which are stronger, have a smoother surface, and produced with a narrower particle size distribution than the granules obtained according to the conventional method.

Stronger granules are very important in the subsequent production steps where it is important that the granules are able to withstand stress so that wear is minimised. Wear will result in fines, which are detrimental to the coating process due to the variability in surface area that they introduce. The fines also result in reduced overall yields.

A smooth surface on the granules is important in order to enable reliable measurement of their surface area and in that way to provide for accurate prediction of the amount of polymer that has to be applied to the granules in order to obtain the right dissolution rate profile. In addition, the reduced surface area of the granules produced according to the present invention allows the amount of coating material to be reduced considerably.

A reproducible particle size distribution for the granules is as important as the two previously mentioned parameters in the control of the coating process. The particle size distribution is defined by the method used to perform the sieve analysis. Equipment that may be used in the analysis may be a number of sieves with different screens placed on top of each other. The mesh of the first screen is bigger than the mesh of the next screen, which is bigger than the mesh of the third screen and so on. An example of meshes that may be used together may be 1400 μm, 1250 μm, 1180 μm, 1000 μm, 850 μm, 710 μm, 600 μm and 500 μm meshes. Thus, an 850-1000 μm fraction is that fraction of the granules that are able to pass the 1000 μm mesh, but not the 850 μm mesh.

Results from the development work show that it actually is possible to obtain granules with the desired properties. Surprisingly, the only change, compared to the existing process, in order to obtain the desired properties, is that the isopropyl alcohol to water ratio of 9:1 used to dissolve the PVP in the existing process, is shifted toward more water. The ratio according to the present invention is 1:1 or less. The primary results, presented in Table 2, showed that the yield is inversely proportional with the isopropyl alcohol content.

Without wanting to be bound by a theory, it is believed that the rough surface and the variable size of the granules prepared by the existing method are due to disruption of the granules during the drying step, caused by explosion-like evaporation of the isopropyl alcohol breaking off large and small pieces of the granules. The rough surface could also be caused by wear of less strong granules in the drying process. It is believed that the use of aqueous granulation in combination with a continuous drying process according to the present invention, leads to a gentler drying of the granules, resulting in stronger granules with a smoother surface.

It is furthermore believed that the improved strength of the granules leads to the possibility of obtaining predefined reproducible particle size distributions.

In addition to obtaining the desired properties of the granules as discussed above, the results also show some benefits with regards to the new production process, namely:

More environmentally acceptable.
The environment in the production area being safer for the operators.
Lower production costs.

The avoidance or reduced use of the organic solvent isopropyl alcohol is a huge advantage both in the handling process, where the operators avoid or minimise the risks related to the use of isopropyl alcohol in the production area, and for the environment in relation to collection and disposal of the isopropyl alcohol during and after drying of the granules. Furthermore, the cost of purchasing and handling isopropyl alcohol is reduced. However, if appropriate, an organic solvent may be added to comprise for up to 50% w/w, however, preferably less than 15% w/w and more preferably less that 5% w/w of the solvent. Most preferred, no organic solvent is used.

Accordingly, the main principles for the manufacturing process of the present invention have not been changed when compared to the existing process. 5-ASA tablets are produced by first mixing the active ingredient, 5-aminosalicylic acid, with a solution of a binder, e.g. polyvinylpyrrolidone in a solvent, which in the present invention is comprised of at least 50% w/w water. Preferably the solvent is free of organic solvent. This wet mass is extruded into granules, which are dried in a continuous fluid bed. After drying, the granules are milled and sieved before the granules are ready for coating in e.g. a fluid bed. In the coating process a polymer is coated upon the granules until the desired dissolution rate profile is obtained. The coated granules are then mixed with tablet excipients and compressed into tablets.

The present invention thus concerns in a first fundamental aspect a method for the preparation of granules comprising 5-aminosalicylic acid (5-ASA) or a pharmaceutically acceptable salt or ester thereof and a pharmaceutically acceptable binder comprising the steps of
(a) dissolving the pharmaceutically acceptable binder in a solvent,
(b) mixing the dissolved binder with 5-ASA to form a wet mass,
(c) extruding the wet mass into granules, and
(d) drying the granules upon evaporation of the solvent,
wherein the new, surprising and advantageous feature is that the solvent is comprised of at least 50% w/w water.

Subsequently, the granules are milled and sieved.

In a preferred embodiment of the invention, the solvent comprises more than 85% w/w water. In another preferred embodiment the solvent comprises more than 95% w/w. Most preferred, the solvent is free of organic solvent. The solvent may optionally comprise one or more additives.

In another preferred embodiment, the resulting granules, after being milled, have a particle size distribution measured by sieve analysis where the main fraction is from 850 µm to 1000 µm. The holes in the extruder may be varied in order to obtain the desired particle size. More than 75%, preferably more than 85% and most preferably more than 90% of the granules have a particle size from 850 µm to 1000 µm.

The ratio of the binder, e.g. polyvinylpyrrolidone, to the active ingredient, 5-ASA, in the resulting granules is preferably up to 8:100, more preferably up to 6.5:100 and most preferably up to 5:100. Other binders, if desired, may replace polyvinylpyrrolidone. Binders that may be considered for the granules are selected from the group comprising derivatives of cellulose, polyvinylpyrrolidone, pregelatinized cornstarch or any other suitable binder. Such binders may be used in different amounts relative to 5-ASA.

In another aspect the present invention utilises the first fundamental aspect in a method for the preparation of prolonged release tablets useful for the treatment of ulcerative colitis or Crohn's disease, comprising the steps of
(a) preparing granules from 5-aminosalicylic acid or a pharmaceutically acceptable salt or ester thereof and up to 8% by weight (solids content, based on the 5-aminosalicylic acid) of a binder in a solvent comprising at least 50% w/w water.
(b) applying onto said granules an polymer composition, comprising a solution in an organic solvent of a pharmaceutically acceptable polymer material thereby to provide coated granules upon evaporation of the solvent,
(c) mixing the coated granules with pharmaceutically acceptable tablet excipients, and
(d) forming tablets from the resulting mixture.

The granules are preferably prepared according to the first aspect of the present invention i.e. the granules are extruded, dried, milled and sieved in one continuous process.

In one embodiment of the method, the granules are dried in a fluid bed.

In another embodiment, the coating material is a cellulose derivative, such as ethyl cellulose.

In a further embodiment, the tablet excipients comprise a tablet carrier, such as microcrystalline cellulose, a lubricant, such as magnesium stearate and optionally further excipients such as talc.

INDUSTRIAL APPLICABILITY

1. General Considerations

As each tablet or dose contains a relative large amount of material, large amounts of material must be handled in the production line. The granules may be manufactured batchwise or in a continuous process, i.e. the granules may be extruded, dried, milled and sieve in one continuous process.

Figure 4:
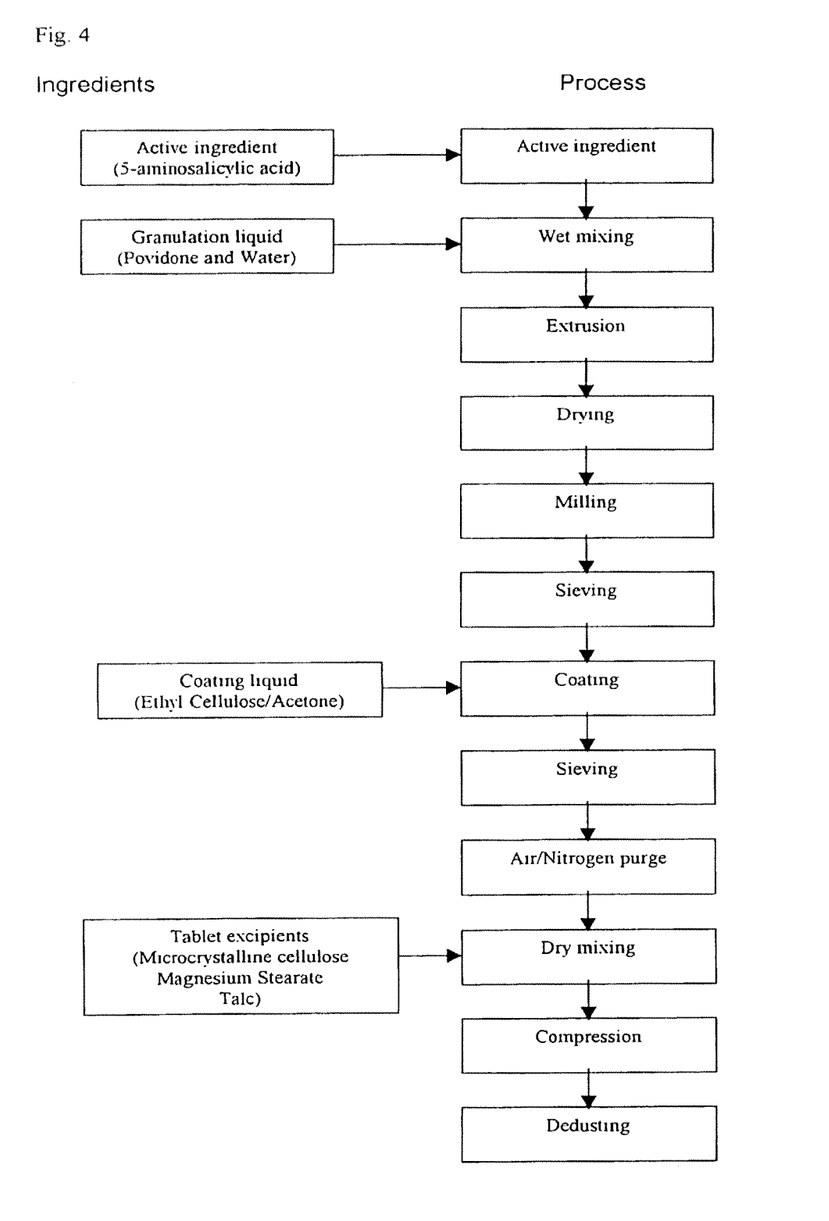
FIG. 4 shows a flow diagram of the new manufacturing process for Pentasa® or similar tablets.
Figure 5A:
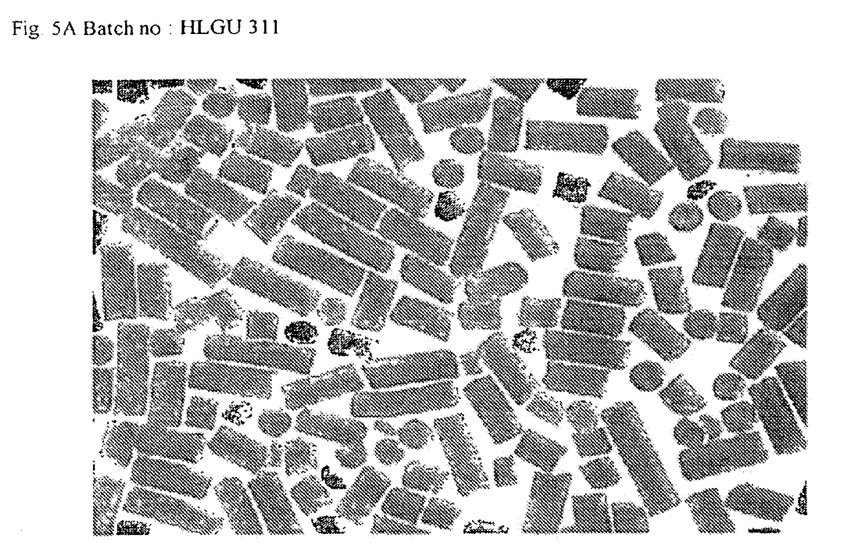
FIG. 5A shows enlarged photo of granules after milling and sieving prepared according to the new process. (Batch no. HLGU311)
Figure 5B:
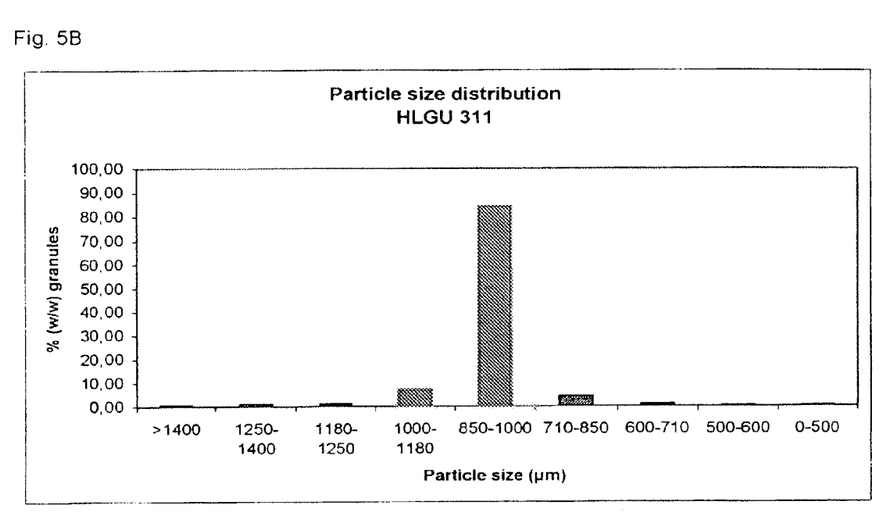
FIG. 5B shows particle size distribution (sieve analysis) after milling and sieving of granules prepared according to the new process. (Batch no. HLGU311)
Figure 6A:
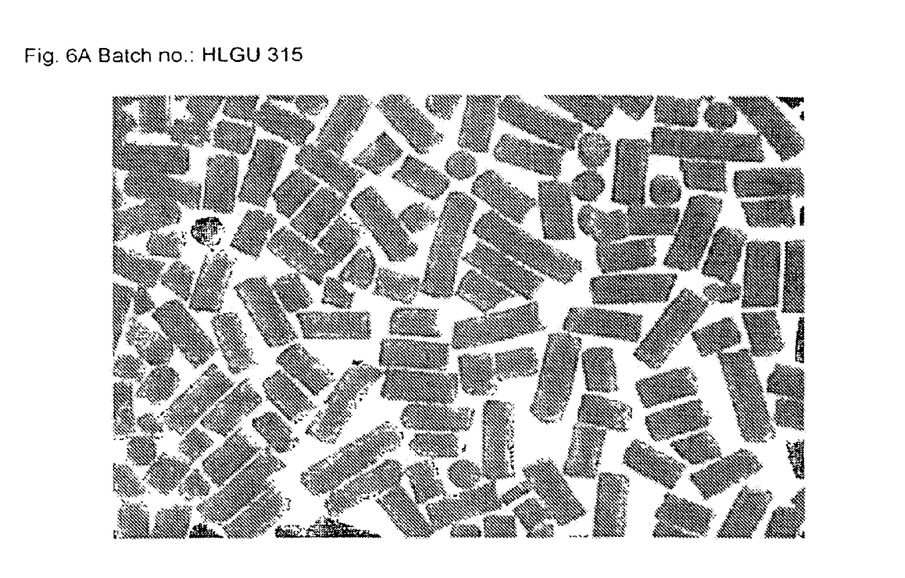
FIG. 6A shows enlarged photo of granules after milling and sieving prepared according to the new process. (Batch no. HLGU315)
Figure 6B:
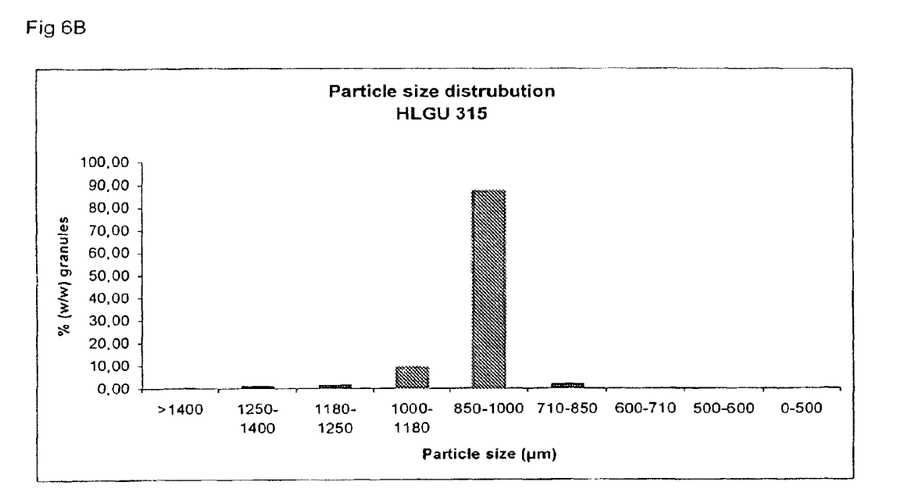
FIG. 6B shows particle size distribution (sieve analysis) after milling and sieving of granules prepared according to the new process. (Batch no. HLGU315)
Figure 7A:
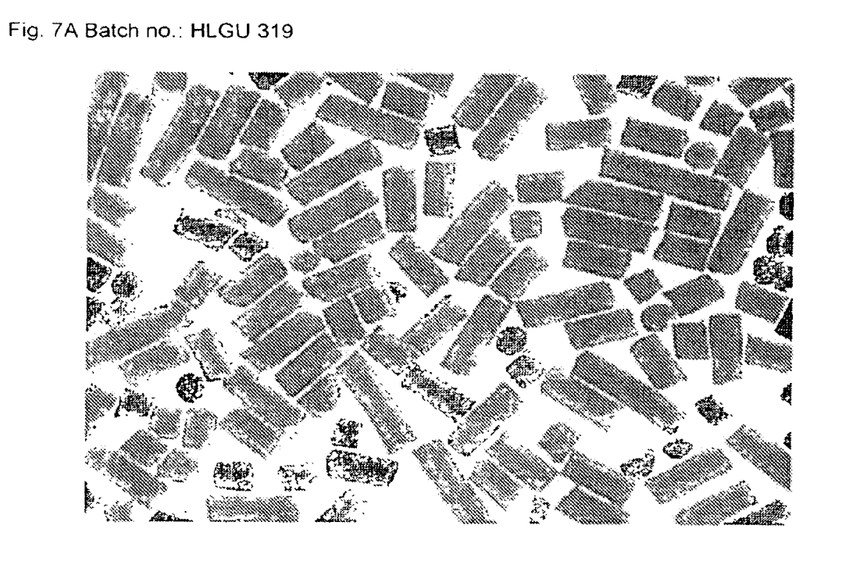
FIG. 7A shows enlarged photo of granules after milling and sieving prepared according to the new process. (Batch no. HLGU319)
Figure 7B:
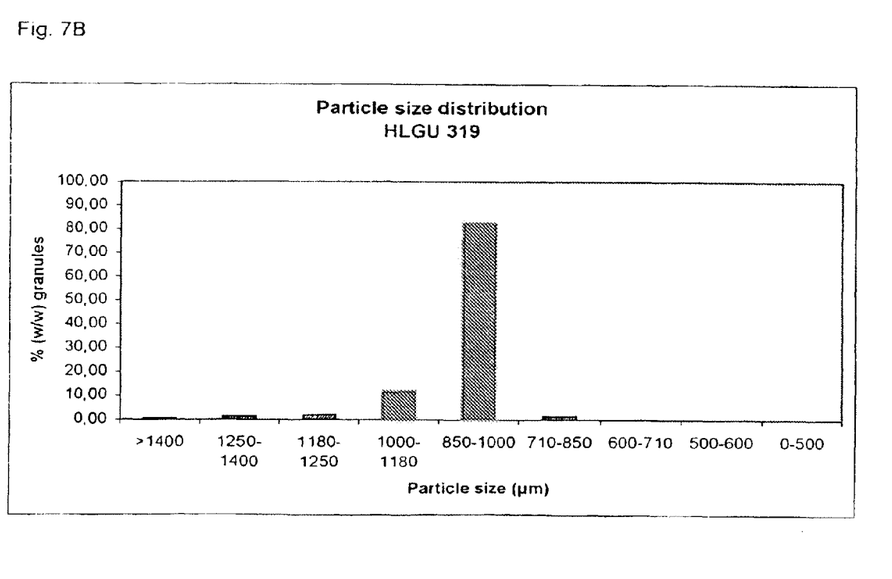
FIG. 7B shows particle size distribution (sieve analysis) after milling and sieving of granules prepared according to the new process. (Batch no. HLGU319)

The production line for the production of granules in a continuous process should be able to handle the following production steps (see also FIG. 4).
1. Wet mixing of 5-ASA with a solution of a binder, such as polyvinylpyrrolidone (Povidone) in water (50% w/w or more)
2. Extrusion
3. Drying
4. Milling
5. Sieving Because it is a continuous process the equipment should be built in such a way that it is possible to control the flow of the different ingredients into the process. By controlling the flow it is possible to get the right ratio between the ingredients through the whole process.

2. Production of Granules Comprising PVP

Polyvinylpyrrolidone (PVP) is dissolved in an solvent, e.g. 100% w/w water. 5-ASA and the aqueous solution of PVP are mixed and added to the extruder. Alternatively, 5-ASA and the aqueous solution of PVP may be mixed in the extruder. The wet mass consisting of 5-ASA and PVP is extruded through a screen and allowed to fall into a device for drying of the wet granules.

The aqueous solvent is preferably water of a suitable quality, but may contain additives, such as chelating agents, antioxidants, reducing agents, buffers and pH adjusting agents.

Advantageously the extruder comprises a screen, which has numerous circular holes with a diameter of between 0.5 and 1.3 mm, preferably 0.9 mm. The thickness of the screen is between 0.9 and 2.0 mm, preferably, the thickness of the screen is 1.5 mm. The holes can have the same cross-section through the screen or be tapered in either direction. Preferably, the holes are tapered, each hole having a cross-section at the inlet side of the sheet that is larger than the cross-section at the outlet side of the screen, the preferred outlet diameter is 0.9 mm and the preferred inlet diameter is 0.95 mm.

Advantageously the drying device is preferably a fluid bed. However, other possibilities known by the skilled person may also be used.

If a fluid bed is used, it may be designed in such a way that the dwelling time in the fluid bed is approximately 2½ hour. However, shorter or longer times are also within the present invention. The fluid bed is advantageously separated in two parts where the granules in the first part are dried on the surface to avoid that they stick together. In this part a random mixing of the granules take place. In the second part of the fluid bed the final drying takes place and the granules are guided through the fluid bed by the pattern of holes in the bottom plate.

When the granules are dry they are discharged from the fluid bed and transferred to a mill to reduce the length of the granules. The milling process generates a small amount of fines that has to be removed by sieving before the granules are ready for coating. At this stage a sieve analysis, as described earlier may be performed.

3. Coating

The resulting granules are coated. The granules may be coated in any coating device applicable to the process. The skilled person would readily know which devices would be suitable for the present process, such as for example a fluid bed system, e.g. a Kugelcoater. The granules are preferably coated with a polymer dissolved in a suitable solvent for the polymer, preferably an organic solvent such as acetone.

In order to be able to determine the amount of polymer that has to be applied to the granules the surface area is measured. Based on a known correlation between the amount of polymer per surface area and the dissolution rate profile, the amount of polymer needed can be predicted from the measured surface area of the granules. The smoother the surface of the granules, the smaller the surface area, and the smaller the surface area, the smaller the amount of polymer needed. Any agglomerates formed during the coating step are removed by sieving.

The selected coating polymer is mostly dependent on the desired release pattern. It may be chosen from rate-limiting barrier-materials, e.g. enteric or delayed coating material, such as polymethacrylat, commercial available in the form Eudragit™ S, Eudragit™ RL and Eudragit™ RS, respectively. When a semi-permeable polymer is used, ethyl cellulose is the most preferred polymer.

4. Mixing

The coated granules are mixed with the remaining tablet excipients in a conventional dry mixing process.

Tablet excipients may include any suitable pharmaceutically acceptable carriers which are well known to the skilled person, e.g. lactose, maize starch, potato starch, and lubricants, e.g. magnesium stearate and talc. A preferred carrier constituent is microcrystalline cellulose.

The Pentasa® tablets produced according to the conventional method comprise as tablet excipients microcrystalline cellulose, magnesium stearate and talc. Tablets according to the present invention may advantageously be comprise the same excipients.

5. Compressing and Dedusting

The final blend of coated granules and excipients is compressed into tablets in any suitable tabletting machine, such as on a rotary tabletting machine and the tablets are dedusted. The tablets may be of any conceivable size or weight, e.g. 100 mg-10 g, more preferably 500 mg to 3 g.

6. The Active Ingredient 5-aminosalicylic acid or any salt or ester thereof is the active ingredient in the granules. The salts of 5-ASA may be acid addition salts, in particular the hydrochloride, but any pharmaceutically acceptable, non-toxic organic or inorganic acid may be used.

Also salts formed with the carboxylic acid group may be used. As examples may be mentioned alkali metal salts (K, Na), alkaline earth metal salts (Ca, Mg), but again any pharmaceutically acceptable, non-toxic salt may be used. The Na- and Ca-salts are preferred.

In DE patent application No. 2712394 (AU application No. 7723548), incorporated herein by reference, a number of esters of ortho-, meta- and para-salicylic acid are disclosed. The disclosed meta- (or 5-) aminosalicylic esters and a number of related esters are also applicable as active ingredient in the composition produced according to the invention.

Applicable esters are e.g. straight chain or branched $C_1$-$C_{18}$ alkyl esters, e.g. methyl, ethyl, propyl, isopropyl, butyl, isobutyl, amyl, hexyl, heptyl, octyl, nonyl, decyl, lauryl, myristyl, cetyl, and stearyl, etc., straight chain or branched $C_2$-$C_{18}$ alkenyl esters, e.g. vinyl, allyl, undecenyl, oleyl, linolenyl, etc., $C_3$-$C_8$ cycloalkyl esters, e.g. cyclopropyl, cyclobutyl, cyclopentyl, cyclohexyl, cycloheptyl and cyclooctyl, etc., aryl esters, e.g. phenyl, toluoyl, xylyl, naphthyl, etc., alicyclic esters, e.g. menthyl, etc., or aralkyl esters, e.g. benzyl, phenethyl, etc.

Generally speaking the proper selection of the active ingredient depends on the selected type of formulation, the disease pattern, especially the site and type of the disease, and the desired release of the active ingredient.

The physical state and solubility characteristics of the 5-ASA derivatives must be taken into account when selecting a suitable carrier composition for the ingredient.

The preferred active ingredient at present is the free acid, 5-aminosalicylic acid.

The effective oral dose depends on the extent of the disease and for adults it usually amounts to 0.5-1.0 g four times a day. Generally about 20 mg/kg body weight of 5-ASA or a salt or ester thereof (calculated as 5-ASA) will be the recommended initial daily dosage subject to adjustment in accordance with the observed results of the treatment.

While the preferred coating agent is ethyl cellulose other coating agents may also be used, provided they secure the desired release pattern. In particular a number of other cellulose derivatives must be assumed to be applicable. At present, the preferred release pattern is a continuous release following arrival in the small intestine. This release was originally designed as to enable the tablets, e.g. Pentasa®, to be effective both against Crohn's disease and ulcerative colitis.

However, in case it should be desirable to secure an early release in the small bowel (in the case of Crohn's disease) or a delayed release until arrival in the colon (in the case of ulcerative colitis), the release pattern can be controlled by varying different parameters of the tablet as discussed in WO 81/02671, which is hereby incorporated by reference.

Example 1

Production of Pentasa Tablets

Existing Isopropanol Based Granulation Process

Pentasa® Slow-Release Tablets 500 mg

| Name of the constituents | Quantity per batch (155000 tablets) | Specifications |
|---|---|---|
| Active ingredient: | | |
| 5-aminosalicylic acid | 77.5 kg | Ferring |
| Other Ingredients | | |
| Povidone | 3875 g ±10% | Ph. Eur. |
| Isopropyl alcohol | 17.3 kg | Ph. Eur. |
| Purified water | 1550 g | Ph. Eur. |
| Ethylcellulose | q.s | Ph. Eur. |
| Acetone | q.s. | Ph. Eur. |
| Magnesium stearate | 155 g | Ph. Eur. |
| Talc | 1395 g | Ph. Eur. |
| Microcrystalline cellulose | ad 116250 g | Ph. Eur. |

Equipment for the Production:

| Equipment | Function |
|---|---|
| NICA Mixer M6L | Granulation |
| NICA Extruder E 220 | Extrusion |
| AEROMATIC Fluid Bed Dryer | Drying |
| FREWITT MG 8 Oscillator | Oscillation |
| MOGENSEN Typ 0254 Sizer | Sieving |
| HÜTTLIN Kugelcoater HKC 200 or | Coating |
| HÜTTLIN Kugelcoater HKC 400 | |
| PRODIMA Mixer AC-HLR 500 | Mixing |
| KILIAN T 300 or | Tabletting |
| KORSCH Pharmapress 250 | |

Manufacturing Steps

The manufacture of Pentasa® Slow-release tablets is performed in 10 steps.

Step 0: Start Routine of the Equipment and Ingredients

All the equipment is checked for cleanliness before use.

Step 1: Weighing 5-aminosalicylic acid is weighed out and fed into the mixer.

Step 2: Granulation

The granulation liquid (povidone dissolved in a mixture of purified water and 2-propanol) is prepared and added during mixing. The mixing is continued for a fixed time after addition of the granulation liquid.

Step 3: Extrusion

The granulated mass is extruded into pellets in the same procedure (Screen 1.0×1.0 (diameter×thickness of the screen)).

Figure 1A:
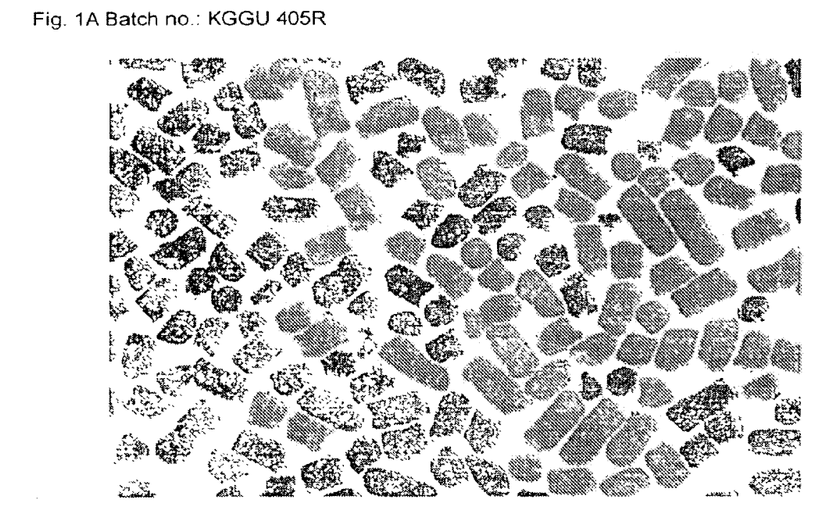
FIG. 1A shows enlarged photo of granules after sieving prepared according to the existing process. (Batch no. KGGU 405R)
Figure 1B:
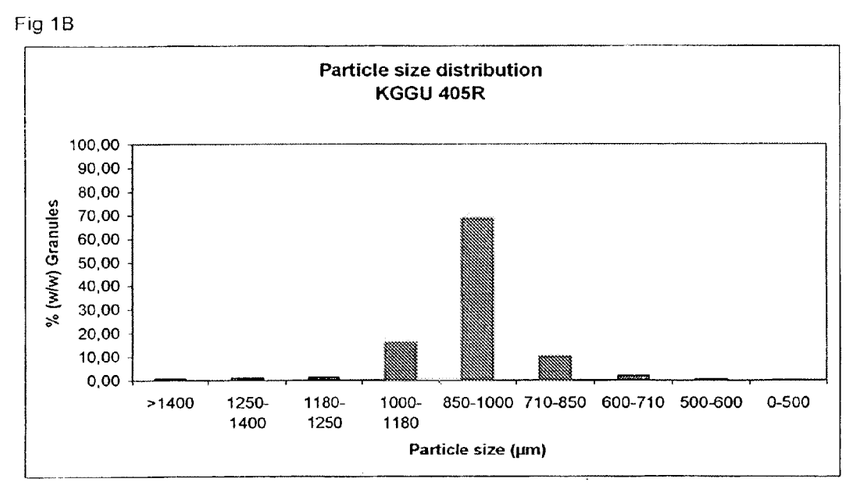
FIG. 1B shows particle size distribution (sieve analysis) after sieving of granules prepared according to the existing process. (Batch no. KGGU 405R)
Figure 2A:
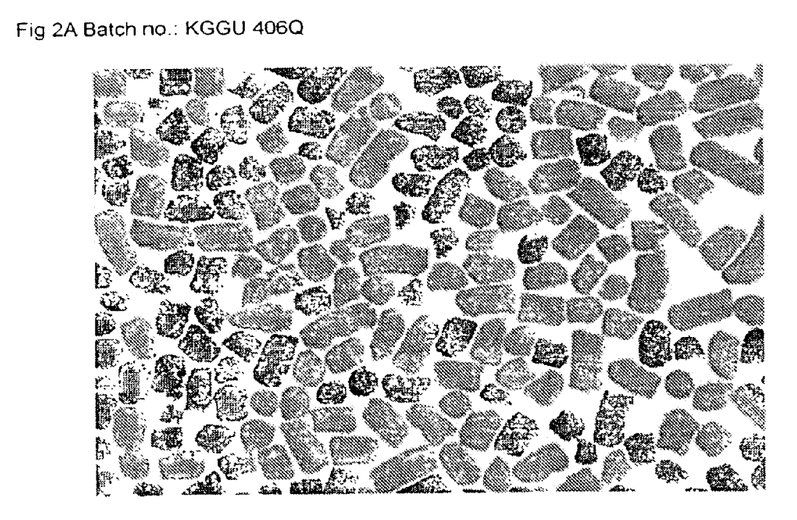
FIG. 2A shows enlarged photo of granules after sieving prepared according to the existing process. (Batch no. KGGU 406Q)
Figure 2B:
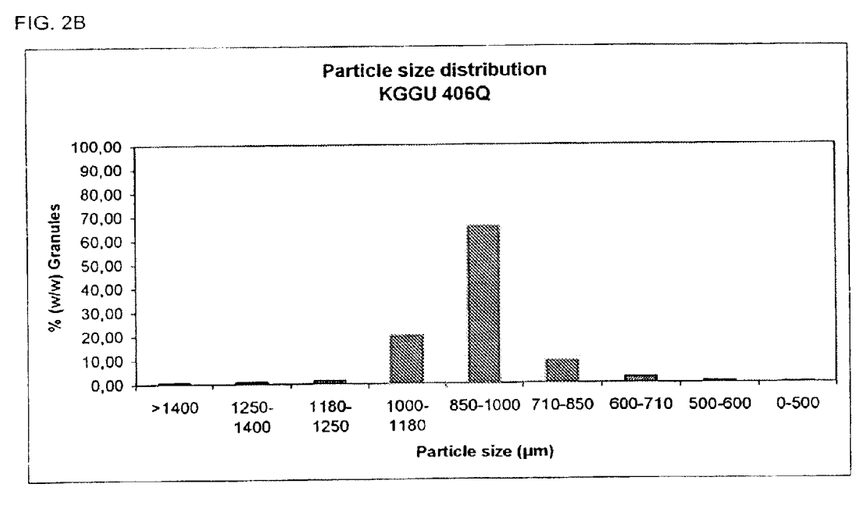
FIG. 2B shows particle size distribution (sieve analysis) after sieving of granules prepared according to the existing process. (Batch no. KGGU 406Q)
Figure 3A:
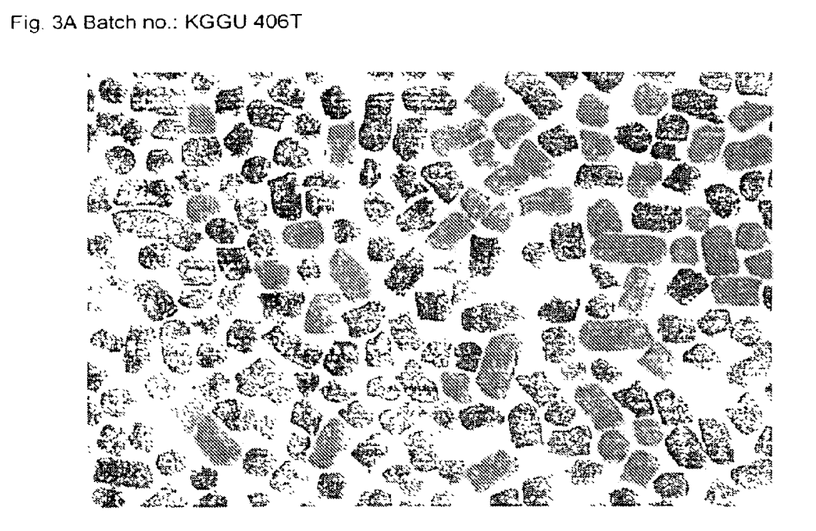
FIG. 3A shows enlarged photo of granules after sieving prepared according to the existing process. (Batch no. KGGU 406T)
Figure 3B:
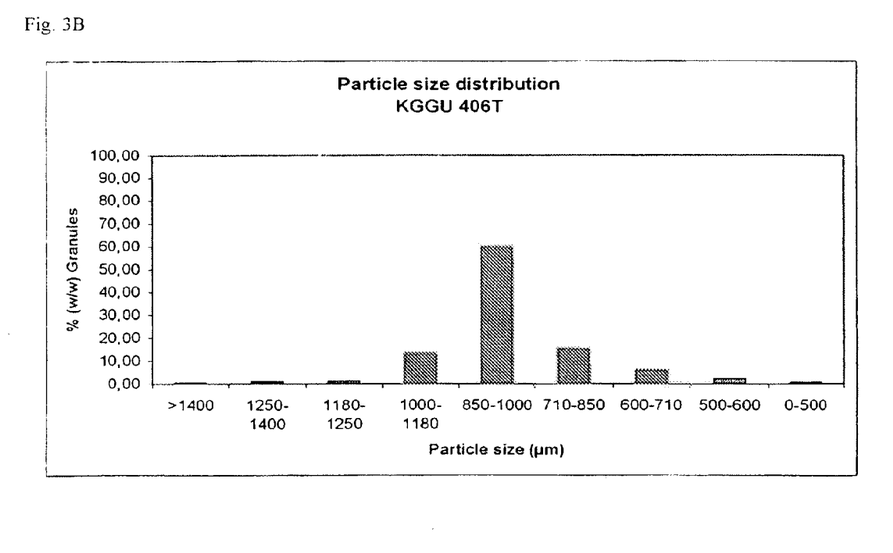
FIG. 3B shows particle size distribution (sieve analysis) after sieving of granules prepared according to the existing process. (Batch no. KGGU 406T)

Step 4: Drying
  The granules are transferred to a fluid bed dryer and dried.
Step 5: Sieving
  The dried pellets are sifted on a Mogensen sieve (tilted sieve). Granules which pass the screen size of 0.8 mm are discarded or can be collected for reprocessing stored in air-tight, labelled containers. Granules which do not pass the screen size of 1.8 mm are discarded.
Step 6: Coating
  The granules are coated in a Kugelcoater (fluid bed system) with a liquid consisting of ethylcellulose in acetone. If any lumps are formed the granules are sifted on a Mogensen sieve (tilted sieve).
Step 7: Mixing
  The coated granules, the filler/binder (microcrystalline cellulose) and the lubricants (magnesium stearate and talc) are transferred to the mixer and thoroughly mixed.
Step 8: Compression
  The final blend of coated granules and lubricants is compressed into tablets on a rotary tabletting machine.
Step 9: Dedusting
  The tablets are deducted.
Step 10: Packaging
  The slow-release tablets are placed in a labelled bulk container and stored in quarantine until released by the Quality Control Department.
  FIG. 1A-3A shows enlarged photos of granules from three different batches obtained by the existing method.

Example 2

The Effect of Variation in Different Parameters of the Process

In the present example dry and wet material were mixed in an Erweka AR 400E Intensive mixer. The extrusion was performed in a Niro Fielder Extruder E140. Unless otherwise stated, the screen used in the extruder contains holes with the dimension 0.9×0.9 mm. (diameter×thickness of the screen). For the sieve analysis is used a Retch Vibro sieve.

At first, 3 critical parameters of the process, the PVP content, the water content and the speed of the mixer were investigated in a $2^3$ factorial analysis:

|  |  | Low level | High level |
|---|---|---|---|
| Factor a | PVP | 3% w/w | 8% w/w |
| Factor b | Water | 0% w/w | 6% w/w |
| Factor c | Impeller | 33 rpm | 66 rpm |

The resulting granules were evaluated as a yield after sieving in the range 0.850-1.0 mm. The test was repeated 5 times and the results show that both the content of water and PVP have influence on the yield in the range 0.850-1.0 mm. The speed of the impeller has no influence on the yield in the given range as shown in table 1:

TABLE 1

Results from the $2^3$ factorial experiment showing the % yield after sieving in the range 0.850-1.0 mm

| Trial | Mean | SD |
|---|---|---|
| (1) | 63.40 | 3.62 |
| a | 60.48 | 2.22 |
| b | 70.22 | 2.12 |
| ab | 80.66 | 3.74 |
| c | 60.68 | 3.59 |

TABLE 1-continued

Results from the $2^3$ factorial experiment showing the % yield after sieving in the range 0.850-1.0 mm

| Trial | Mean | SD |
|---|---|---|
| ac | 66.38 | 4.52 |
| bc | 70.44 | 2.21 |
| abc | 80.22 | 3.00 |

In order to optimise the content of water and PVP in the extruded granules a new trial was conducted in 2 repetitions. The water plus isopropyl alcohol (IPA) was kept constant at 35% w/w, and the water content varied between 6, 12 and 18% w/w. The PVP content was varied between 5, 6.5 and 8% w/w.

The results are shown in table 2 and show that the higher content of water, the higher yield was obtained. If the content of PVP was increased to 8% w/w, the yield decreased due to agglomerates.

Encouraged by the above results, yet another trial was set up to investigate what would happens if the water content was further increased and the IPA omitted. The solvent (water+IPA) content was again kept constant at 35% w/w, while the water content was varied between 24, 30 and 35% w/w. In addition, solvent contents of 30 and 33% w/w, free of IPA were used in the trial. The PVP content was varied between 5 and 6.5% w/w As shown in table 2, if the amount of water is increased to 30% w/w and the IPA omitted, a higher yield of granules is obtained.

TABLE 2

% Yield as a function of water content and amount of PVP.

|  |  | % w/w PVP | | |
|---|---|---|---|---|
|  |  | 5 | 6.5 | 8 |
| % w/w Water | 6 | 72.8 | 78.1 | 82.9 |
|  | 12 | 78.0 | 82.7 | 48.3 |
|  | 18 | 80.3 | 82.7 | 42.9 |
|  | 24 | 80.0 | 85.5 |  |
|  | 30 | 84.8 | 89.6 |  |
|  | 30 no IPA | 93.7 | 94.2 |  |
|  | 33 no IPA | 94.9 | Too wet |  |
|  | 35 no IPA | Too wet |  |  |

The Effect of the Screen on the Resulting Granules

In order to optimise the holes in the extruder, different screens were tried out. The results shown in table 3, indicate that for the selected wet mass, 0.9×0.9 mm (diameter×thickness of screen) was the best choice for obtaining granules with a particle size of 850-1000 μm.

TABLE 3

Particle size distribution as a function of hole dimensions in the screen.

|  |  | Hole dimensions mm | | | |
|---|---|---|---|---|---|
|  |  | 1.0 × 1.2 | 1.0 × 1.0 | 0.9 × 1.0 | 0.9 × 0.9 |
| Particle size μm | >1180 | 2.0% | 1.7% | 1.0% | 0.7% |
|  | 1000-1180 | 78.2% | 57.0% | 4.5% | 1.4% |
|  | 850-1000 | 17.1% | 39.2% | 58.6% | 92.8% |
|  | <850 | 2.7% | 2.2% | 35.9% | 5.2% |

In a repeated trial, the narrow and reproducible particle size distribution of the granules prepared according to a preferred method of the present invention was investigated and shown in table 4.

TABLE 4

Particle size distribution of batches prepared according to a preferred method of the present invention.

| Batch no.: | >1180 µm | 850 µm < x < 1180 µm | <850 µm | % (w/w) moisture |
|---|---|---|---|---|
| 732902 | 2.2 | 92.8 | 4.7 | 0.56 |
| 733101 | 1.1 | 94.2 | 5.7 | 1.14 |
| 733102 | 0.9 | 94.2 | 5.2 | 0.99 |
| 733103 | 0.8 | 94.1 | 5.4 | 0.53 |
| 733104 | 1.0 | 94.2 | 5.3 | 0.46 |
| 733107 | 2.2 | 94.5 | 4.6 | 0.50 |
| Mean | 1.4 | 94.0 | 5.2 | 0.51 |
| SD | 0.65 | 0.60 | 0.42 | 0.04 |
| RDS | 48 | 0.64 | 8.1 | 8.3 |

The moisture content was also of an acceptable level.

For practical use of the screen in a production facility, a thickness of the screen of 1.5 mm is preferred.

The strength of the granules was evaluated by processing the granules 1 hour in a laboratory fluid bed (STREA). The strength was compared to granules produced in accordance with the existing production facilities for producing Pentasa®. As shown in table 5, the strength is increased in the granules produced in accordance with the present invention:

TABLE 5 showing the % of granules with a particle size between 850 µm-1000µm before and after processing the granules in a laboratory fluid bed for 1 h.

| | Batch No. | Before Strea | After Strea | Difference |
|---|---|---|---|---|
| Present invention | 733102 | 94.2 | 95.2 | −1.0 |
| | 733103 | 93.9 | 94.1 | −0.2 |
| | 733104 | 93.9 | 94.6 | −0.7 |
| | 733107 | 94.8 | 93.9 | 0.9 |
| Existing process | EJGU838C | 57.5 | 54.9 | 2.6 |
| | EJGU838D | 63.5 | 60.9 | 2.6 |
| | EJGU837G | 68.5 | 61.9 | 6.6 |
| | EJGU838H | 53.3 | 44.6 | 8.7 |

Example 3

Production of 5-ASA Comprising Tablets

Water Based Granulation Process

The new manufacturing process for the 5-ASA tablets can be divided into 11 steps (FIG. 4):
1. Preparation of granulation liquid
2. Granulation of 5-ASA with water and PVP
3. Extrusion
4. Fluid bed drying
5. Milling
6. Sieving
7. Coating
8. Sieving
9. Air purging
10. Dry blending with excipients
11. Compression to tablets Equipment for the Production

| | |
|---|---|
| NICA Extruder E220 | Extrusion |
| Rotostat T05 | Blending |
| NIRO Fluid bed dryer | Drying |
| Quadro Comil U10 | Milling |
| Mogensen sieve | Sieving |
| Huttling Kugelcoater HKC 400 | Coating |
| Prodima rotation sieve | Sieving |
| Purging unit | Air purge |
| Prodima Mixer AC-HLR 1200 | Dry mixing |
| Kilian T300-32 | Tabletting |

Step 1:

For one batch of granulation liquid 118.4 kg of water is filled into a Müller drum. The mixer is put into position and started. 32 kg of polyvinylpyrrolidone (PVP) is slowly sprinkled onto the water and the mixer is allowed to run a fixed time until all PVP is dissolved.

Step 2 and 3:

5-ASA is placed in a vibrating Prodima hopper and by the use of a conveyor the 5-ASA is transported up to a weight belt feeder dosing the 5-ASA into the continuous Niro line. In the first part of the Niro line the 5-ASA and the water solution of PVP are mixed to a wet mass before being transported into the extruder. After extrusion of the wet mass of 5-ASA and PVP/water through a screen mesh 0.9 mm, the granules fall directly into the fluid bed dryer.

Step 4:

The fluid bed dryer is divided into two main sections. In the first section, the granules are dried on the surface to prevent them from sticking together. In this section of the fluid bed, a random mixing of the granules takes place. After a certain residence time, the granules are moved into the second part of the dryer where the actual drying takes place. In the second part of the dryer the granules are guided by the use of the drying air through the dryer (special pattern of holes in the gill plate). When the granules are dry they are allowed to fall into a drum placed under the fluid bed. The fluid bed is constructed in such a way that the overall dwelling time in the fluid bed is approximately 2½ hour.

Due to the property of being a continuous process, the batch size is defined by how long time the equipment is running. The equipment is therefore built in a way making it possible to control the flow of the different ingredients going into the process. In order to document the drying process, the results from loss on drying are shown in table 6.

TABLE 6

Loss on drying (% moisture in the granules after drying)

| Müller drum | AAA137 | AAA138 | AAA139 | AAA140 |
|---|---|---|---|---|
| 1 | 0.40 | 0.34 | 0.37 | 0.37 |
| 2 | 0.37 | 0.30 | 0.40 | 0.40 |
| 3 | 0.46 | 0.29 | 0.37 | 0.37 |
| 4 | 0.33 | 0.40 | 0.40 | 0.33 |
| 5 | 0.37 | 0.39 | n.a. | 0.37 |
| 6 | n.a. | 0.29 | n.a. | 0.33 |
| 7 | n.a. | 0.34 | n.a. | 0.33 |
| 8 | n.a. | 0.37 | n.a. | 0.39 |
| Mean | 0.37 | 0.39 | 0.39 | 0.36 |

(n.a. = not available)

Step 5:

The drums containing the dry granules are placed upside down on top of the mill and the granules are gently milled using a screen, which will only break the granules that are too long. After passing the mill, the granules are allowed to fall into a drum. FIG. 5A-7A show enlarged photos of three different batches of granules produced according to the present invention. A difference in shape, conformity and homogeneity can be clearly seen when compared to the granules produced according to the existing process (FIG. 1A-3A).

Step 6:

Due to the fact that the milling process generates a small amount of undersized granules, the granules are sieved using a Mogensen vibration sieve. Granules, which pass the screen 0.8-mm, are discarded or can be collected for reprocessing stored in air-tight, labelled containers.

Results from sieve analysis of the milled and sieved granules are shown in FIG. 5B-7B.

Step 7:

200 kg of sieved granules are coated in a Kugel coater (fluid bed system) with a coating liquid consisting of ethyl cellulose dissolved in acetone.

In order to be able to determine the right amount of polymer necessary to apply on the granules to get the desirable dissolution rate profile, the surface area of the granules are measured prior to the coating process. The prediction of the quantity of polymer that is necessary to apply on the granules has been developed based on the fact that there is a correlation between the amount of polymer per surface area and the dissolution rate of the granules. After finishing the coating process, the coated granules are loaded into a drum for further processing.

Step 8:

After the coating process, the coated granules are sieved in a Prodima rotation sieve. Large lumps are discarded.

Step 9:

After sieving the batch of coated granules, they are divided into two drums for purging with compressed air or nitrogen. The granules are purged for 6-14 hours. This purging process is necessary to reduce the amount of residual solvent (acetone) in the coated granules.

Results from test of residual solvent in granules prepared according to the existing method and according to the new method are shown in table 7. As seen from table 7 the content of residual solvent has been reduced considerably in the granules manufactured according to the new method. This may ascribed to the fact that these granules have a smoother surface than the granules prepared by the existing method, hence the amount of coating material necessary is reduced.

TABLE 7

Residual solvent in coated Pentasa ® granules.

|  | Amount of Acetone before purging with Air/Nitrogen (ppm) | Amount of Acetone after purging with Air/Nitrogen (ppm) |
|---|---|---|
| Existing method Pentasa ® granules Batch no. | | |
| GIGC 905 | 5277 | 2607 |
| GIGC 906 | 5556 | 1870 |
| GIGC 907 | 4310 | 1798 |
| New method Pentasa ® granules Batch no. | | |
| AAF 333 | 965 | 331 |
| AAF 322 | 1125 | 402 |
| AAF 327 | 1020 | 492 |

Step 10

178.56 kg coated Pentasa granules are weighed out and loaded into the Prodima blender together with 69.34-kg microcrystalline cellulose. After mixing for 210 seconds the blender is stopped. 0.335 kg magnesium stearate and 3.02 kg Talc are added to the blend and the ingredients are mixed for 90 seconds. The blend will give 335.000 tablets.

After mixing the blend is discharged into Müller drums ready for compression.

Step 11

The final blend of coated granules and excipients is compressed on a rotary tabletting machine. Weight of the tablets: 750 mg. Dedusting of the tablets is performed as an in line process with the tabletting machine. After dedusting the tablets, they are loaded into bulk containers holding approximately 30.000 tablets each.

The method of the present invention leads to an increased overall yield of 5-ASA tablets from the same amount of ingredients as obtained by use of the existing method. The properties of the tablets from 10 batches prepared according to the present invention are shown in table 8.

As can be seen from these tables, the tablets prepared according to the present invention comply with criteria for acceptance of the tablets and the overall yield is about 85.5% compared to 69.2% for the existing method.

Figure 8:
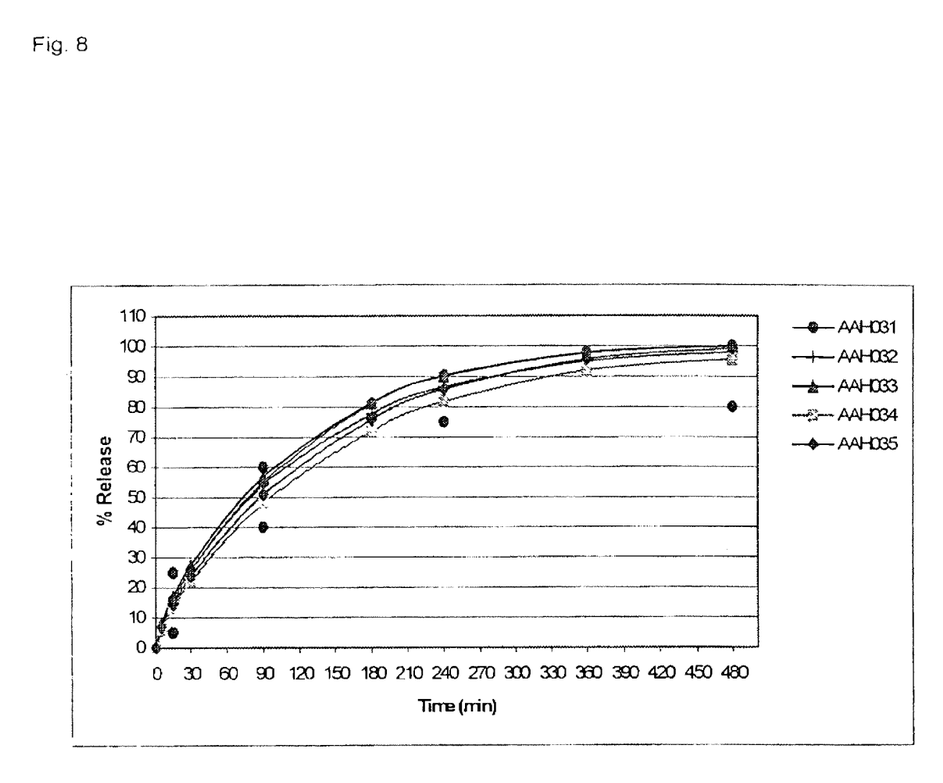
FIG. 8 shows dissolution rate profiles for Pentasa® tablets prepared according to the present invention. The figure shows the release specifications that the applicant has established for the product in order to be allowed for sale.

Dissolution rate profiles for Pentasa® tablets are shown in FIG. 8

Figure 9:
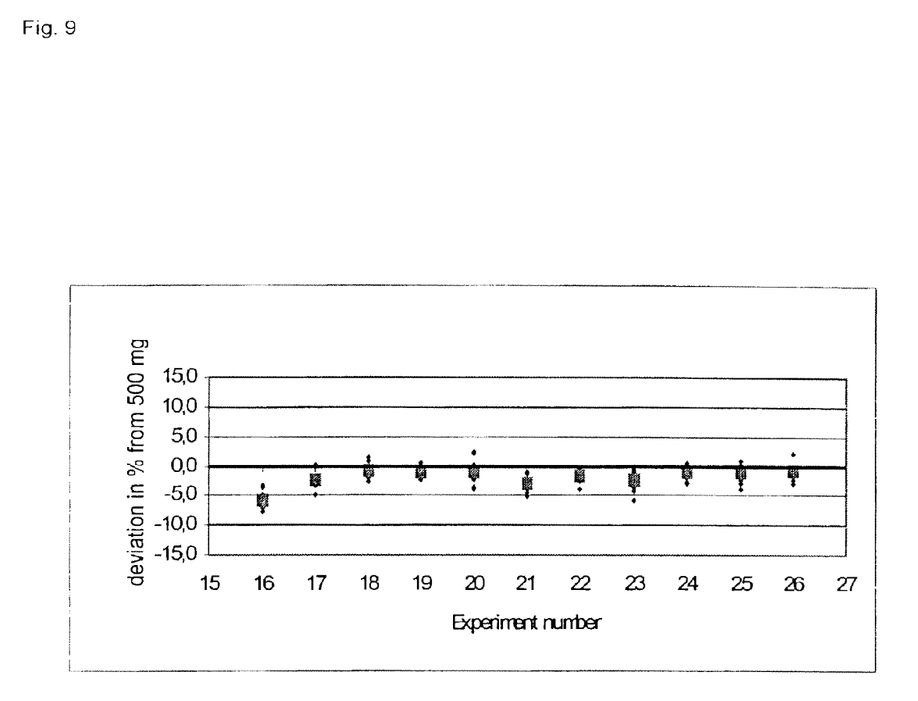
FIG. 9 shows samples taken in the blender to document homogeneity of the blend.

FIG. 9 shows the results of samples taken in the blender to document homogeneity of the blend.

TABLE 8

Test results from 10 batches of Pentasa ® tablets

| Tablet Batch | Hardness N | Weight mg | Height mm | Disintegration sek | Content uniformity mg | Weight variation mg | Assay mg/tabl | Friability % |
|---|---|---|---|---|---|---|---|---|
| AAH025 | 98 | 749.1 | 4.10 | 10 | 520.0 | 515.8 | 507.0 | 0.03 |
| | | | | | 491.4 | 498.9 | | |
| AAH026 | 100 | 751.5 | 4.04 | 11 | 523.9 | 509.2 | 503.8 | 0.05 |
| | | | | | 497.8 | 498.4 | | |
| AAH027 | 80 | 750.8 | 3.97 | 5 | 512.3 | 495.7 | 492.4 | 0.20 |
| | | | | | 486.6 | 487.8 | | |
| AAH028 | 99 | 751.4 | 4.04 | 8 | 514.5 | 498.4 | 489.3 | 0.07 |
| | | | | | 483.7 | 486.7 | | |
| AAH030 | 97 | 748.1 | 4.00 | 8 | 511.6 | 495.1 | 497.1 | 0.03 |
| | | | | | 486.0 | 487.2 | | |
| AAH031 | 92 | 750.9 | 3.98 | 9 | 509.9 | 508.9 | 502.2 | 0.04 |
| | | | | | 481.4 | 496.8 | | |

TABLE 8-continued

Test results from 10 batches of Pentasa ® tablets

| | | | | | | | | |
|---|---|---|---|---|---|---|---|---|
| AAH032 | 96 | 751.6 | 3.97 | 11 | 507.3 485.9 | 499.9 492.6 | 495.9 | 0.08 |
| AAH033 | 99 | 753.1 | 4.02 | 9 | 516.6 495.3 | 506.4 499.0 | 504.4 | 0.03 |
| AAH034 | 103 | 749.1 | 4.00 | 9 | 513.6 467.3 | 500.9 488.4 | 495.0 | 0.04 |
| AAH035 | 97 | 749.8 | 4.08 | 7 | 531.1 487.9 | 493.8 485.2 | 491.8 | 0.04 |
| Acceptance criteria | 84-112 average of 10 | 735-765 average of 10 | 3.80-4.20 average of 10 | ≤5 min average of 6 | 425-575 each tablet | 425-575 each tablet | 450-550 average of 20 | ≤0.8% average of 10 |
| Result | Comply | Comply | Comply | Comply | Comply | Comply | Comply | Comply |

The invention claimed is:

1. A method for the preparation of granules comprising 5-aminosalicylic acid (5-ASA) or a pharmaceutically acceptable salt or ester thereof, comprising:
   (a) mixing polyvinyl pyrrolidone as a pharmaceutically acceptable binder in a solvent, the solvent consisting of at least 85% w/w water and up to 15% w/w organic solvent, to form a solvent-binder mixture;
   (b) mixing the solvent-binder mixture with 5-ASA to form a wet mass consisting of 5-ASA, binder, and solvent, in which the solvent is present in amount up to 35% by weight of the weight of 5-ASA;
   (c) extruding the wet mass to form strong, smooth granules comprising 5-ASA and binder; and
   (d) drying the granules in a continuous fluid bed dryer to produce dried granules in which the weight ratio of the binder to 5-ASA is up to 6:5:100 and more than 85% of the dried granules have a particle size of 850 to 1000 μm.

2. A method according to claim 1, further comprising:
   (e) coating the dried granules with a solution of a pharmaceutically acceptable coating material in an organic coating solvent, wherein the amount of the coating solution is adjusted to the specific surface are of the dried granules to achieve the desired dissolution rate profile.

3. A method according to claim 2, wherein the coating material is selected to provide a dissolution rate-limiting barrier on the granules.

4. A method according to claim 2, wherein the coating material comprises ethyl cellulose.

5. A method according to claim 3, wherein the barrier is semipermeable.

6. A method according to claim 1, wherein more than 90% of the dried granules have a particle size of 850 to 1000 μm.

7. Granules comprising 5-aminosalicyclic acid (5-ASA) or a pharmaceutically salt or ester thereof, made by the method of claim 1.

8. Granules comprising 5-aminosalicyclic acid (5-ASA) or a pharmaceutically salt or ester thereof, made by the method of claim 2.

9. A tablet comprising 5-aminosalicylic acid (5-ASA) or a pharmaceutically salt or ester thereof, formed using granules made by the method of claim 1.

10. A tablet comprising 5-aminosalicylic acid (5-ASA) or a pharmaceutically salt or ester thereof, formed using granules made by the method of claim 2.

* * * * *